(12) United States Patent
Koenig et al.

(10) Patent No.: US 7,892,837 B2
(45) Date of Patent: Feb. 22, 2011

(54) METHOD FOR TRANSFERRING MOLECULES IN VITAL CELLS BY MEANS OF LASER BEAMS AND ARRANGEMENT FOR CARRYING OUT SAID METHOD

(75) Inventors: Karsten Koenig, Hyazinthenweg 18, D-66119, Saarbruecken (DE); Uday Krishna Tirlapur, Oxford (GB)

(73) Assignee: Karsten Koenig, Saarbruecken (DE)

( * ) Notice: Subject to any disclaimer, the term of this patent is extended or adjusted under 35 U.S.C. 154(b) by 643 days.

(21) Appl. No.: 10/515,558

(22) PCT Filed: May 22, 2003

(86) PCT No.: PCT/DE03/01708

§ 371 (c)(1),
(2), (4) Date: Mar. 3, 2006

(87) PCT Pub. No.: WO03/100069

PCT Pub. Date: Dec. 4, 2003

(65) Prior Publication Data

US 2006/0141624 A1    Jun. 29, 2006

(30) Foreign Application Priority Data

May 23, 2002 (DE) ................................ 102 23 921
May 23, 2002 (DE) ................................ 102 23 922

(51) Int. Cl.
    *C12N 15/87* (2006.01)
(52) U.S. Cl. .................. 435/460; 435/285.1; 435/173.5
(58) Field of Classification Search ........................ None
See application file for complete search history.

(56) References Cited

PUBLICATIONS

Denton et al., Investigative Ophthamology & Visual Science, vol. 47, 2006, pp. 3065-3073.*
Stephens, et al.: The many ways to cross the plasma membrane, *Proc. Nat. Acad. Sci. USA*, 89 (2001) 4295-4298.
Luo, et al.: Synthetic DNA delivery systems, *Nature Biotechnol.* 18 (2000) 33-37.
Bildirici, et al.: Transfection of cells by immunoporation, *Nature* 405 (2000) 298.
M. Knoblauch et al.: A galinstan expansion femtosyringe for microinjection of eukaryotic organelles and prokaryotes, *Nature Biotechnol.* 17 (1999) 906-909.

Tsukakoshi, et al.: A Novel Method of DNA Transfection by Laser Microbeam Cell Surgery, *Appl. Phys.* B35 (1984) 135-140).
Kurato et al. : The Laser Method for Efficient Introduction of Foreign DNA into Cultured Cells, (*Exp. Cell Res.* 162 (1986) 372-378.
Weber, et al.: Microperforation of Plant Tissue with a UV Laser Microbeam and Injection of DNA into Cells, *Natur wissenschaften* 75 (1988) 36).
Greulich: "Micromanipulation by light in biology and medicine", Birkhäuser Verlag, 1999.
Tao et al.: Direct gene transfer into human cultured Cell Facilitated by Laser micropuncture of the Cell Membrane, (*PNAS* 84 (1987) 4180-4184).
Denk, et al.: Two-Photo Laser Scanning Fluorescence Microscopy, *Science* 248 (1990) 73).
XP002257731 / Plant Journal, bD20, Nr. 3, Nov. 1999, pp. 363-370, Tirlapur, et al, "Near-Infrared femtosecond laser pulses as a novel non-invasive means for dye-permeation and 3D imaging of localised dye-coupling in the Arabidopsis root meristem".
XP002257732 / Histochemistry and cell biology, Germany 2000, Bd. 114, Nr. 2, Aug. 2000, pp. 79-92, K. Koenig, "Robert Feulgen Prize Lecture. Laser tweezers and multiphoton microscopes in life sciences".
XP002257733 / Journal of Microscopy, England Nov. 2000, Bd. 200 (pt 2) Nov. 2000, pp. 83-104, K. Koenig, "Multiphoton microscopy in life sciences".
XP002257734 / Experimental Cell Research, Bd.263, Nr. 1, (Feb. 1, 2001), pp. 88-97, Tirlapur, et al., :Femtosecond near-infrared laser pulses elicit generation of reactive oxygen species in mammalian cells leading to apoptosis-like death.
XP002257735 / Nature, England Jul. 28, 2002, Bd.418, Nr. 6895 Jul. 18, 2002), pp. 290-291, Tiralpur, et al., :Targeted transfection by femtosecond laser.

* cited by examiner

*Primary Examiner*—James S Ketter
(74) *Attorney, Agent, or Firm*—Frommer Lawrence & Haug LLP

(57) ABSTRACT

The invention relates to an optical method for targeted transfer of molecules, preferably of DNA, RNA, peptides, amino acids and proteins, into vital cells by means of laser radiation and to an arrangement for implementing the method. The object of the invention, to find a novel possibility for targeted molecule transfer into the interior of vital cells, particularly the transfer of DNA, RNA, peptides, amino acids and proteins, which achieves a high transfer efficiency while extensively excluding destructive side effects such as a lethal effect on a treated cell, is met according to the invention in that cellular membranes are opened transiently for the molecule transfer by multiple laser pulses in the microjoule range or less and a pulsed, near-infrared laser beam with a pulse width in the femtosecond range is directed in each instance to a submicrometer spot of a membrane of the vital cell for an irradiation period of less than one second.

17 Claims, 2 Drawing Sheets

METHOD FOR TRANSFERRING MOLECULES IN VITAL CELLS BY MEANS OF LASER BEAMS AND ARRANGEMENT FOR CARRYING OUT SAID METHOD

CROSS-REFERENCE TO RELATED APPLICATIONS

This application claims priority of PCT Application Serial No. PCT/DE03/01708, filed May 22, 2003, German Application No. 102 23 922.3, filed May 23, 2002 and German Application No. 102 23 921.5, filed May 23, 2002, the complete disclosure of which is hereby incorporated by reference.

BACKGROUND OF THE INVENTION a) Field of the Invention

The invention is directed to an optical method for the targeted transfer of molecules, preferably DNA, RNA, peptides, amino acids and proteins, into vital cells by means of laser radiation and to an arrangement for implementing the method.

The method is advantageously suitable for the transfection of plant cells, animal cells and human cells, for example, for producing drugs such as synthetic vaccines.

By means of the arrangement according to the invention, the method can be used effectively for the transfection of genes in individual cells and opens up applications in the fields of plant materials and animal materials production, gene therapy and in the production and application of specific drugs, particularly synthetic vaccines.

b) Description of the Related Art

Targeted molecule transfer plays an important role in the production of vaccines, among other things. Vaccines are used within the framework of active immunization of humans and animals for stimulating the immune system against pathogenic microorganisms and pathogenic substances. Normally, inactivated or attenuated germs which still retain an immunogenic effect are used. A slight health risk is involved in activating individual attenuated germs. This may have fatal consequences particularly for patients with weakened immune defense. Considerably more critical, however, is the fact that there is currently no vaccine available for many diseases, including AIDS. Methods in gene technology aim at making possible the production of effective, highly-pure synthetic vaccines through DNA transfer. The implantation of foreign DNA in plants and animals for expressing vaccines in foodstuffs is being discussed. In principle, a specific immunity against very particular amino acid sequences can be achieved.

The transporting of foreign DNA to a target cell can be carried out by means of specific carriers, e.g., colloidal particles such as nanospheres and microspheres, emulsions and liposomes. Virus-like aggregates (VLA) in which the molecules to be transported are enclosed by a two-layer membrane are currently being researched.

When colloidal particles of this kind are applied intravenously, for example, they are normally intercepted with high efficiency by the reticuloendothelial system (Kupffer cells, etc.) and, therefore, cannot effect the transfer to the actual target. In order to prevent this unspecific binding, the surface of the particles is changed, e.g., through determined coatings and suitable particle sizes, by means of complicated particle engineering. Finally, when the target cell in the target organ is reached more or less effectively and selectively, problems arise with respect to particle reception and there is a risk of destruction through lysosomal enzymes and nucleases.

Therefore, an efficient foreign DNA accumulation in the cytoplasm or directly in the cell nucleus of a specific target cell is desirable.

The targeted transfer of molecules, preferably of DNA into vital cells, was carried out heretofore:

(i) by mechanical processes such as microinjection and particle gun bombardment;

(ii) by means of biological (viruses, bacteria, etc.) and synthesized carrier molecules; or (iii) by permeabilizing the membrane by means of electrical fields (electroporation) or chemical agents (e.g., streptolysin O toxin).

There are problems with all three of these methods with respect to the efficiency of the molecule transfer and the high probability of an unintended lethal effect as is confirmed by the prior art mentioned in the following.

It is known (e.g., D. J. Stephens, R. Pepperkok: The many ways to cross the plasma membrane, *Proc. Nat. Acad. Sci. USA*, 89 (2001) 4295-4298; D. Luo, W. M. Saltzman: Synthetic DNA delivery systems, *Nature Biotechnol.* 18 (2000) 33-37; L. Bildirici, P. Smith, C. Tzavelas, E. Horefti, D. Rickwood: Transfection of cells by immunoporation, *Nature* 405 (2000) 298) to carry out a transfer of molecules, preferably of DNA, into vital cells by means of synthesized carrier molecules and biological carrier systems (viruses, etc.).

It is likewise known to enable the targeted transfer of molecules through mechanical methods such as microinjection and particle gun bombardment (e.g., M. Knoblauch et al.: A galinstan expansion femtosyringe for microinjection of eukaryotic organelles and prokaryotes, *Nature Biotechnol.* 17 (1999) 906-909).

Further, the transfer of molecules into vital cells by permeabilization of the membrane by means of electrical fields (electroporation) or chemical agents (e.g., streptolysin O toxin) is known.

In conventional vaccine production using gene technology, cell cultures are typically infected with viruses, as carriers of the DNA in question, under strict safety measures in bioreactors; the viruses are then inactivated or attenuated.

The direct transfer of individual molecules in a specifically selected individual cell is only possible by means of mechanical microinjection using thin glass cannulas (typical distal diameter: 0.5 mm) through invasive disruption of the cell membrane; this process is inefficient and entails a high potential of injury. Mechanical gene transfer by manual microinjection requires specially trained personnel and is met by considerable difficulties when transferring into nonadherent cells, in plant cells because of the sturdy cell wall, and with isolated protoplasts. In addition, the presence of the glass in the interior of the cell causes considerable problems due to the adherence of intracellular molecules, e.g., certain proteins. The occurring mechanical forces result in additional destructive effects.

Optical methods for targeted molecule transfer based on focused laser radiation through the microablation of a membrane section were carried out heretofore by means of ultraviolet laser sources with pulse widths in the nanosecond range and high energy in the microjoule and millijoule range. Laser pulses with such long pulse widths generate collateral destructive mechanical effects through intensive photodisruptive processes. In addition, the application of ultraviolet radiation is controversial due to cytotoxic and mutagenic effects. UV radiation is also absorbed outside the focus area by a plurality of endogenic molecules. Accordingly, the success rate of this type of optical transfection is low. Testing of laser-assisted gene transfer has been conducted since 1984 (Tsukakoshi et al. (1984) *Appl. Phys.* B35 135-140). Normally, ultraviolet (UV) nanosecond lasers with a relatively high pulse energy in the µJ range and single-shot mode are used. The transfection rates are very low, as is confirmed in the literature by Tsukakoshi et al. (*Appl. Phys.* B35 (1984) 135-140) and Kurato et al. (*Exp. Cell Res.* 162 (1986) 372-378) which shows transfection efficiencies of a maximum 0.6%. Tsukakoshi et al. describe an arrangement for the transfer of genes which is based on a frequency-tripled 10 Hz Nd:YAG nanosecond laser at a working wavelength of 355 nm and which is outfitted, in addition, with a He—Ne laser as pilot laser and enables beam deflection through the use of two galvoscanners. An image of the sample is displayed on a TV monitor by means of a transillumination apparatus using an UV blocking filter and is recorded by means of video recorders. Single shots with high pulse energies of 1 mJ were used for perforating the cell membrane.

Nitrogen lasers with an emission wavelength of 337 nm were also used for gene transfer in plant cells (Weber et al.: *Naturwissenschaften* 75 (1988) 36). In UV laser-assisted gene transfer in plant embryos, a transformation efficiency of 0.5% was reported (Greulich: "Micromanipulation by light in biology and medicine", Birkhäuser Verlag, 1999).

Another publication by Tao et al. (*PNAS* 84 (1987) 4180-4184) describes UV exposure with µJ pulses with a pulse duration of 10 ns in a relatively large irradiation area of 2.0-µm diameter using an inverted Zeiss microscope with a 32× objective. At this magnification, the numerical aperture is typically less than 0.8. The relatively large irradiation spot involved probably caused a considerable perforation in the membrane on the same order of magnitude. The transformation efficiency in these tests using human cells was less than 0.3%.

In sum, it can be stated that there are no known methods or apparatus usable in practice for transferring molecules, particularly for the production of synthetic vaccines, into a specially selected individual cell efficiently and effectively without damaging the living cell.

OBJECT AND SUMMARY OF THE INVENTION

It is the primary object of the invention to find a novel possibility for targeted molecule transfer into the interior of vital cells, particularly the transfer of DNA, RNA, peptides, amino acids and proteins, which achieves a high transfer efficiency while extensively excluding destructive side effects, such as a lethal effect, on a treated cell.

According to the invention, this object is met in a method for transferring molecules into vital cells by means of laser radiation, preferably for targeted transfer of DNA, RNA, peptides, amino acids and proteins into vital cells and for the transfection of plant cells, animal cells and human cells, particularly for the production of drugs such as synthetic vaccines, in that the cellular membranes are opened transiently for the molecule transfer by multiple laser pulses in the microjoule range or less, wherein a pulsed, near-infrared laser beam with a pulse width in the femtosecond range is directed to a submicrometer spot of a membrane of the vital cell for an irradiation period of less than one second.

Multiple laser pulses with a pulse repetition frequency in the MHz range or higher are advantageously used for laser irradiation. Laser pulses with energies in the nanojoule range are preferably used. The laser pulses are advisably adjusted in such a way that a mean light intensity in the TW/cm$^2$ range is achieved in the laser spot on the membrane of the target cell.

It has proven advantageous for accuracy and for spatially limiting the transient membrane permeability for molecular transfer to focus the laser beam on a submicrometer spot in a diffraction-limited manner.

Further, for purposes of the technical implementation of the method according to the invention in an arrangement for targeted transient molecule transfer into vital cells by means of a laser beam, particularly for the transfer of DNA, RNA, peptides, amino acids or proteins, in which the molecules are moved from an extracellular environment through an optically increased permeability of a membrane into the interior of an individual cell, with a laser whose laser beam is focused on the cell with a short pulse duration, the above-stated object is met in that the laser is a mode-synchronized solid state laser with an emission in the wavelength range of 700 nm to 1200 nm, this laser being constructed as a pulse laser for generating multiple femtosecond pulses with a pulse duration of less than 500 fs and pulse energies in the microjoule range or less, in that focusing optics are provided for preparing a diffraction-limited submicrometer spot, wherein a light intensity in the terawatt per square centimeter range on the biological membrane of a target cell is adjustable in the spot, in that a shutter for generating processing times of microseconds to a second is arranged in front of the laser, and in that devices for aligning and observing the target cells are provided, wherein an additional illumination source, imaging optics, special filters and a CCD camera for finding and aligning a target cell and for detecting laser-induced, highly localized transient membrane changes is directed to the spot exposed by the laser, and a sample stage that is movable in three dimensions is provided for submicrometer-exact positioning of the target cell relative to the laser spot and for focusing by means of a z-adjustment unit.

The illumination source, in combination with the imaging optics and CCD camera for target finding, target positioning and observation of the transient membrane change, advantageously has a beam for transmitted light illumination, preferably of white light.

In another advantageous variant, the illumination source has a beam for fluorescence excitation. Endogenic fluorophores (autofluorescence) or preferably exogenic (administered) fluorophores (e.g., fluorescing membrane markers) can be excited in this way.

Further, it has proven advisable when the laser beam is used at the same time for two-photon excited fluorescence of a fluorescing membrane marker.

The laser beam advantageously has a pulse energy of less than 100 nm in the laser spot on the target cell.

For sample handling with respect to the orientation of the laser spot on an individual target cell and a selected membrane surface, the laser beam is focused on a fixed point; the positioning of the laser beam relative to the target membrane is provided by means of the sample stage and the focus control is provided by means of the z-adjustment unit of the objective.

The shutter is advantageously switchable between a first opening state for providing nanojoule pulses for membrane processing and a second opening state for providing picojoule pulses for observing the beam position.

In order to detect the position of the laser beam with respect to the target cell, the CD camera is advantageously outfitted with a filter so that small portions of the laser beam reflected or transmitted by the target cell or its carrier are imaged on it and, further, has computer elements and control elements for showing the laser spot portion simultaneously with the imaging of the target cell generated by the beam of the additional illumination source.

The image processing unit downstream of the CCD camera advisably has a computer with special image processing software for identifying target cells.

The computer is advantageously connected at the same time to control units and adjusting units for controlling the sample stage. The information about target cells that is obtained from the object identification is provided for selecting and positioning the target cell and for focusing the laser.

The control units and adjustment units are advisably provided on the basis of the object identification supplied by the computer for positioning a selected membrane of the target cell in the laser focus.

Further, the image processing unit advantageously contains image processing software by which the course of the transient membrane changes can be detected. Accordingly, the successful molecule transfer can be detected and the search and processing of the next target cell can be initiated automatically.

The basic idea of the invention consists in opening a membrane of a vital target cell (prokaryot, eukaryot) transiently for the molecule transfer through laser exposure with multiple laser pulses in the millijoule or nanojoule energy range in a submicrometer spot over an irradiation period of less than one second. In this way, in addition to the external cell membrane, other intracellular membranes, e.g., the nuclear envelope, can be treated in a targeted manner.

It has been shown that by applying special laser irradiation of this kind a laser-induced, highly localized transient membrane change through cancellation of the barrier function in the area of the laser spot makes possible a temporary efficient transfer of molecules in the cell and, therefore, an efficient transfection without this molecule transfer being accompanied by destructive side effects. The destructive side effects mentioned in the beginning, such as phototoxic effects and low transfection efficiency, do not occur.

The invention will be described more fully in the following with reference to an embodiment example.

DESCRIPTION OF THE PREFERRED EMBODIMENTS

Figure 1:
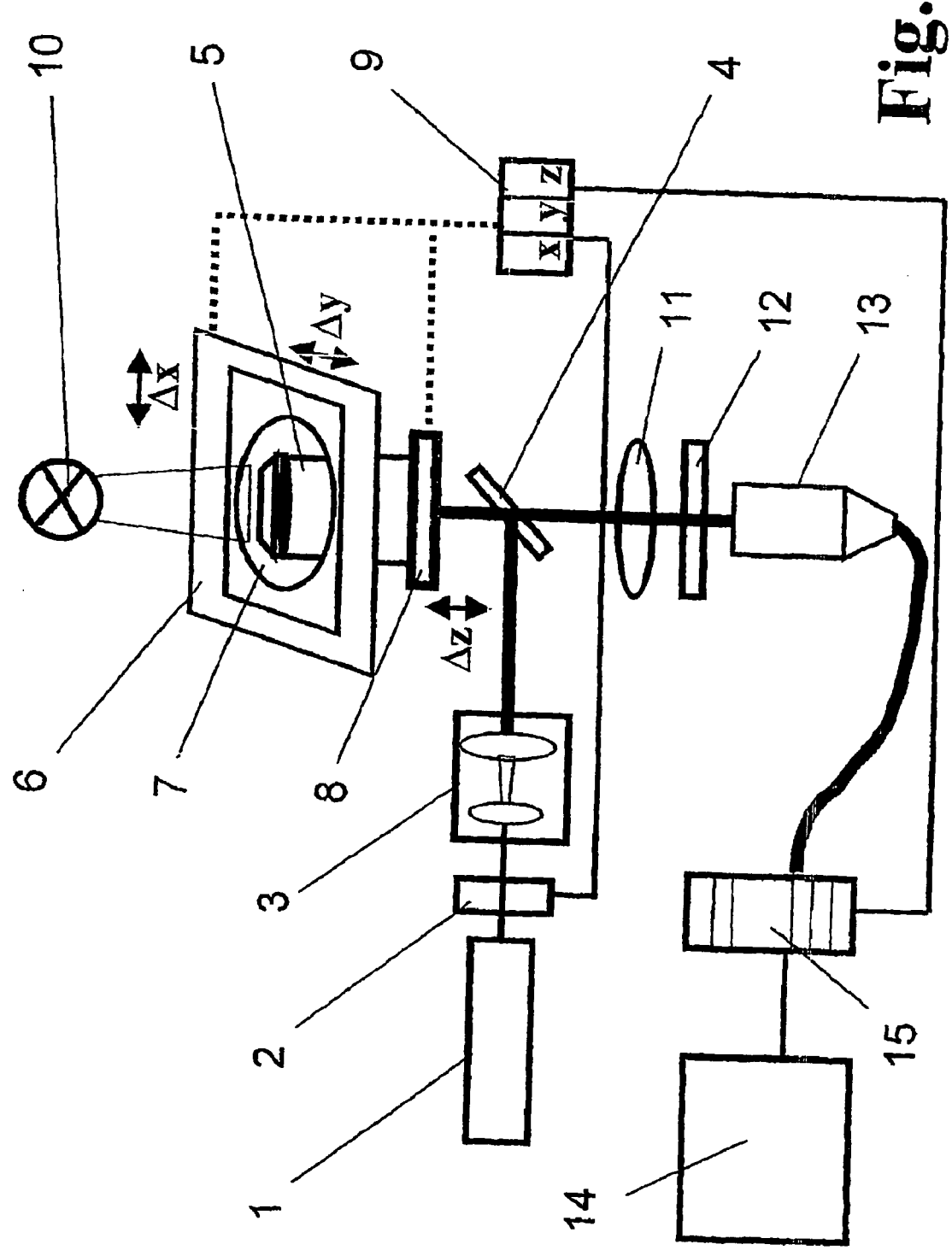
FIG. 1 is a schematic view of the arrangement according to the invention.

The invention is described with respect to its process flow—without limiting generality—with reference to an arrangement shown schematically in FIG. 1.

The arrangement basically comprises a laser 1 with a shutter 2 and beam expander 3 arranged in front of it, an objective 5, a motor-operated sample stage 6 with target cells 7 located thereon, which motor-operated sample stage 7 supports the target cells so as to be movable relative to the laser spot generated by the objective 5 by means of a z-adjustment unit 8 of the objective 5 and an x,y,z-adjustment unit 9, an additional illumination source 10, and a CCD camera 13 for recording an image of the treated target cells 7 that is generated by the illumination source 10.

A mode-synchronized 80-MHz titanium-sapphire laser, as laser 1, is coupled into a laser scanning microscope and is focused in a diffraction-limited manner on a submicrometer spot by means of a 40× objective 5 having the high numerical aperture of 1.3. The mean output at a pulse width of about 200 fs is initially a few microwatts for observing and searching the target cell. First, a cell layer of CHO cells (Chinese hamster cells), a cell layer of PTK cells (rat kangaroo cells) and a cell layer of adult human DPSC stem cells were applied by means of a scanner and an image was generated based on the transmitted beam and detection by means of a photomultiplier. In individual cases, the two-photon excited fluorescence signal of a fluorescing membrane marker can also be used for image generation. The cells are usually located in a miniaturized sterile cell chamber containing 0.5 ml of culture medium and 0.2 μg of plasmid DNA vector pEGFP-N1 (4.7 kb). This plasmid causes the synthesis of green fluorescing protein.

The laser beam is subsequently focused on a selected submicrometer area of the membrane of an individual selected cell (scanner in point-irradiation mode) and the output is increased to between 50 mW and 100 mW. The area is irradiated by means of a fast beam shutter for 16 ms. Subsequent scans at a reduced average microwatt output showed the existence of a transient membrane change (membrane eversion) in the area of the selected membrane area of the target cell struck by the laser spot. An irradiation of this kind probably causes the temporary microperforation of the cell membrane through which the plasmid can penetrate into the cell.

The irradiation mode was tested repeatedly on 200 cells. The time required for transfection through cell searching, beam focusing and irradiation was typically 10 to 15 seconds.

The integration of the DNA plasmid and the expression of the green fluorescing protein was investigated in situ by stationary, time-resolved two-photon fluorescence imaging at an average laser output of less than 1 mW over a duration of 72 hours. The successful laser-induced expression of EGFP was confirmed by measuring the mean fluorescence lifetime of ~2.4 ns. Regardless of cell type, it was possible to achieve a transfection rate and an expression rate of more than 90% as is shown impressively in FIG. 2.

The arrangement, according to the invention, for efficient molecule transfer into an individual vital cell preferably contains a mode-synchronized femtosecond laser with a high repetition frequency which is determined in the wavelength range between 700 nm and 1200 nm and, by means of an objective 5 with a high numerical aperture (greater than 0.8), provides a laser beam of multiple nanojoule laser pulses which is focused on a submicrometer spot in a rigidly fixed and diffraction-limited manner with a light intensity in the $TW/cm^2$ range for transient cancellation of the barrier function of biological membranes in the area of the laser spot. Further, the arrangement comprises a fast shutter 2 which realizes irradiation periods in the microsecond and millisecond range using nanojoule pulses and picojoule pulses for target adjustment, an additional illumination source 10, imaging optics 11, special filter 12 and CCD camera 13 for finding and adjusting the target and for detecting laser-induced, highly localized transient membrane changes, a preferably motor-operated sample stage 6 with submicrometer accuracy, a z-adjustment unit 8, an image processing unit 15 with object identification and control modules for automated transfer of DNA, RNA and proteins into vital individual cells.

A femtosecond laser scanning microscope such as is known for applications in the field of cell biology (see, e.g., Denk et al. *Science* 248 (1990) 73) is preferably used. In contrast to a beam deflection (with special scanning optics, beam guidance and controls) that is usually carried out by means of a (costly) galvoscanner, the beam of the femtosecond laser is localized on a fixed point by means of beam expander 3, deflecting unit 4 and objective 5 for scanning the samples according to the invention. The scanning and focusing regimen is realized solely by means of the motor-operated sample stage 6 and the adjustment units 8 and 9.

In a preferred construction in FIG. 1, a pulsed solid state laser with high beam quality ($TEM_{00}$ mode), an emission wavelength of 800 nm, high repetition frequency (with typical values of around 80 MHz), a pulse duration of less than 300 fs, and a pulse energy of a few nanojoules (<100 nJ) is used as laser 1 for efficient molecule transfer. With a fast shutter 2 with minimum switching times in the microsecond range, the laser beam can be released virtually without losses for treating the target cell 7 or can be blocked between 95% and 99% for the detection of the laser beam position in the target cell 7 before striking the expander 3. The beam is then deflected to the focusing optics 5 with a numerical aperture of greater than 0.8, typically 1.2, by the deflecting mirror 4 (with a NIR reflectivity between 90% and 99%) and accordingly focused on a diffraction-limited submicrometer spot inside the sample 7 located on the sample stage 6.

The sample, e.g., a vital cell—or, more simply, as target object: target cell 7—is advisably located in a miniature cell chamber with at least one glass window with a thickness of about 170 μm. The target cell 7 is typically surrounded by a medium which also contains molecules to be transferred, e.g., determined DNA plasmids. The laser beam is focused through the glass window on a membrane section of the target cell 7. This membrane section can be the cell membrane, a cell wall, the membrane of an organelle or the nuclear envelope.

The focusing plane can be changed in depth (z-direction) with an accuracy of less than 100 mm by means of a piezo-driven z-adjustment unit 8. All three directions x, y, z of the positioning table 6 can be adjusted by the associated adjusting unit 9 with submicrometer accuracy (e.g., with integrated joystick).

The illumination source 10 of low light intensity ensures an imaging of the target cell 7 also during laser irradiation through the combination with imaging optics 11, short-pass filter 12, which causes a sharp attenuation of the laser radiation, and CCD camera 13. The actual position of the laser spot, in addition to the visualization of transmitted light of the illumination source 10, is received in such a way that the laser beam reflected at the target cell 7 and/or its glass carrier can be displayed with high spatial precision in the central portion of the monitor 14 as a bright, non-halated laser spot together with the image of the target cell 7 generated by the illumination source 10. A computer, preferably a PC, as image processing unit 15 with control unit and regulating unit and an image analysis program for object identification (pattern recognition system) makes it possible to detect the target membrane and the automated displacement of the sample stage 6 and z-adjustment unit 8 in such a way that a part of the target membrane and the laser focus coincide. In fully-automatic or semi-automatic operation, the shutter 2 is controlled immediately after target adjustment and a large number of nanojoule laser pulses are applied to a membrane of the target cell 7 for irradiation periods of less than one second. Simultaneously and shortly after successful laser irradiation, a transient change in the membrane in the form of an eversion may be observed on the monitor 14. Normally, these membrane changes cease after several seconds to several minutes. Immediately after irradiation, the membrane is permeable to molecules and enables the transfer of DNA, RNA and proteins in a particularly effective manner. When the transient change is detected by the image analysis program, a new target, usually a new target cell 7, is automatically adjusted by actuating the adjustment unit 9 by means of the control module and the process described above is repeated. When no transient change in the membrane is detected in the area of the irradiated field, the adjustment is carried out on a neighboring membrane region of the same cell and laser irradiation is carried out again.

In the simplest case, the irradiation source 10 works with white light. However, it can also emit fluorescence excitation radiation instead of white light, which makes it possible to detect fluorescing membrane markers by means of CCD camera 13. The laser 1 itself can be used as a fluorescence excitation source by means of two-photon effects. In addition, the described arrangement can also be integrated in a microscope.

By target membrane is meant not only cell membranes or cell walls, but also intracellular membranes such as nuclear envelopes and mitochondrial membranes.

Figure 2:
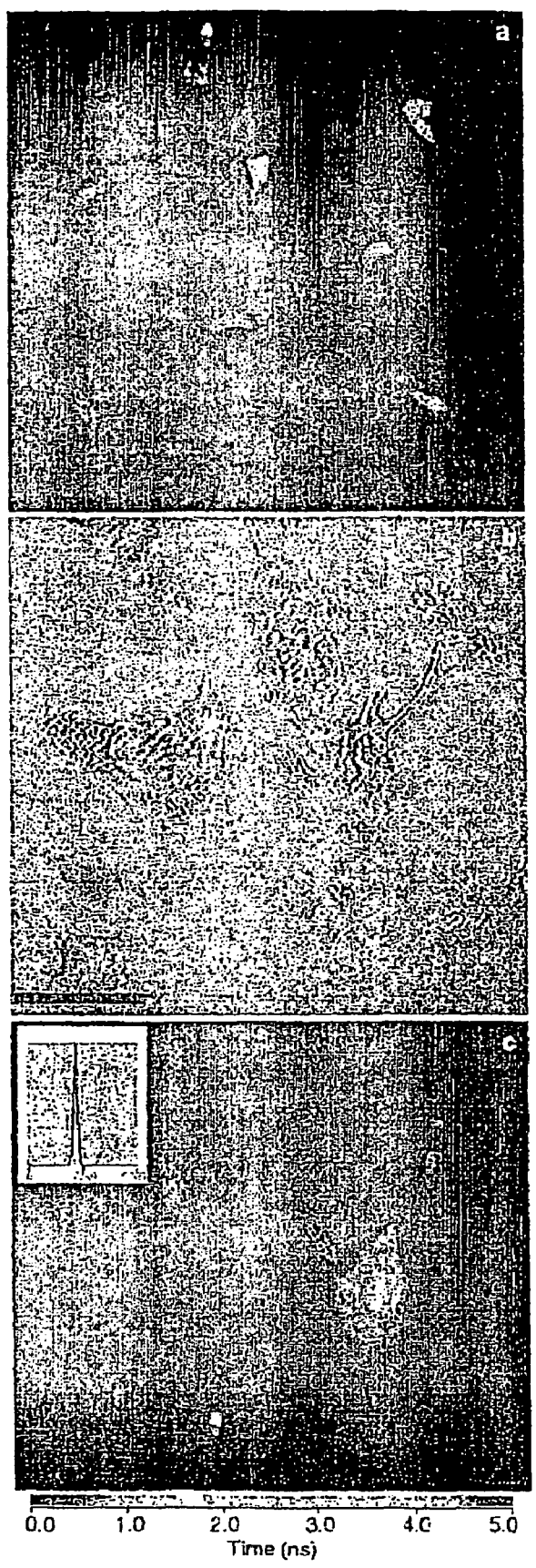
FIG. 2 illustrates the successful transfection of CHO cells with pEGFP-N1 in the form of an image acquisition of the expression a few hours after irradiation by the intensive femtosecond pulses with CCD recordings of single-photon and two-photon fluorescence imaging and NIR transmission imaging.

FIG. 2 shows the successful transfection of CHO cells with pEGFP-N1 and the image recording of the expression several hours after irradiation with the intensive femtosecond pulses through NIR transmission recording, two-photon fluorescence imaging and CCD display. The partial images (scale: bar=25 μm) show:

a: a real EGFP fluorescence image by means of a CCD camera after single-photon blue excitation; a number of fluorescing cells can be seen after successful laser transfection;

b: a NIR transmission image with an arrow indicating the individual cells worked by the laser; and c: a two-photon fluorescence lifetime image in which the individual fluorescing cell can be seen clearly after the laser processing; surrounding cells which were not irradiated with the intensive laser pulses do not fluoresce significantly; the calculated fluorescence lifetime of 2.4 ns corresponds to the expected value for the green fluorescing protein (GFP).

While the foregoing description and drawings represent the present it will be obvious to those skilled in the art that various changes may be made therein without departing from the true spirit and scope of the present invention.

REFERENCE NUMBERS 1 laser
2 shutter
3 expander
4 deflecting mirror
5 objective
6 sample stage
7 target cell (sample)
8 z-adjustment unit
9 adjustment unit
10 (additional) illumination source
11 imaging optics
12 short-pass filter
13 CCD camera
14 monitor
15 image processing unit

What is claimed is:

1. A method for transferring molecules into vital cells by means of laser radiation, comprising the steps of:

directing a near-infrared laser beam of a titanium-sapphire laser to a submicrometer spot on a cellular membrane of the vital target cell; wherein the near-infrared laser beam is pulsed with a pulse width of at least 1 fs and less than 500 fs; and irradiating the cellular membrane of the vital target cell with multiple laser pulses of at least 1 nJ and less than 1 mJ for an irradiation period of at least 1 μs and less than one second to open the cellular membrane transiently for the targeted molecule transfer of DNA, RNA, peptides, amino acids, or proteins into the vital target cell.

2. The method according to claim 1;
wherein multiple laser pulses with a pulse repetition frequency of at least 1 MHz is used.

3. The method according to claim 1;
wherein said multiple laser pulses are applied with energies of at least 1 nJ and less than 1 μJ.

4. The method according to claim 1;
wherein the laser pulses are applied with a light intensity of at least 1 TW-cm$^2$ and less than 1 PW-cm$^2$.

5. The method according to claim 1;
wherein the laser beam is focused to the submicrometer spot on the cellular membrane in a diffraction-limited manner.

6. An apparatus for DNA, RNA, peptide, amino acid or protein molecule transfer into vital cells by means of a laser beam, in which the molecules are moved from an extracellular environment through an increased permeability of a membrane into the interior of a cell, comprising:

a laser for generating a pulsed near-infrared laser beam with a pulse width of at least 1 fs and less than 1 ps, the laser being a mode-synchronized solid state laser with an emission in the wavelength range of 700 nm to 1200 nm;

wherein the laser is constructed as a pulse laser for generating multiple femtosecond pulses with pulse durations of less than 500 fs and pulse energies of at least 1 nJ and less than 1 mJ;

focusing optics for focusing the laser beam to a diffraction-limited submicrometer spot, wherein a light intensity of at least 1 TW-cm$^2$ and less than 1 PW-cm$^2$ on the biological membrane of a target cell is adjustable in the spot;

a quick shutter for generating processing times of the laser beam on the membrane of the target cell, the shutter being disposed in the laser beam path, whereby the interaction of the multiple laser pulses to the cellular membrane is limited to time periods in at least 1 μs and less than one second to merely transiently open the membrane for the molecule transfer of DNA, RNA, peptides, amino acids or proteins; and devices for aligning and observing the target cells, including at least an additional illumination source, imaging optics, filters, and a CCD camera for finding and aligning a target cell and for detecting laser-induced, localized transient membrane changes within the spot exposed by the laser; and a movable sample stage being provided for submicrometer-exact positioning of the target cell relative to the laser spot and for focusing by a z-adjustment unit.

7. The apparatus according to claim 6;
wherein the illumination source, in combination with the imaging optics and CCD camera for target searching, target positioning control and observation of the transient membrane change, has a beam for transmitted light illumination.

8. The apparatus according to claim 6;
wherein the illumination source has a beam for fluorescence excitation, wherein endogenic fluorophores (autofluorescence) or exogenic fluorophores can be excited.

9. The apparatus according to claim 6;
wherein the laser beam is simultaneously used for two-photon excited fluorescence of exogenic fluorophores.

10. The apparatus according to claim 6;
wherein the laser beam is focused on a fixed point, wherein the positioning of the spot relative to the target membrane is provided by means of the sample stage and the focusing control is provided by means of the z-adjustment unit of the sample stage.

11. The apparatus according to claim 6;
wherein the laser beam has a pulse energy of less than 100 nJ in the laser spot on the membrane of the target cell.

12. The apparatus according to claim 11;
wherein the shutter is switchable between a first opening state for providing nanojoule pulses for membrane processing and a second opening state for providing picojoule pulses for observing the beam position.

13. The apparatus according to claim 6;
wherein the CD camera is outfitted with a filter so that small portions of the laser beam reflected or transmitted by the target cell or by a carrier of the target cell are imaged on it and has an image processing unit for showing the laser spot simultaneously with the imaging of the target cell generated by the beam of the additional illumination source.

14. The apparatus according to claim 6;
wherein the image processing unit downstream of the CCD camera has a computer with image processing software for identifying target cells.

15. The apparatus according to claim 14;
wherein the computer is connected to control units and adjusting units for controlling the sample stage, wherein the information from the image processing and the object identification is provided for selecting and positioning the target cell and for focusing the laser.

16. The apparatus according to claim 15;
wherein the control units and adjustment units are provided on the basis of the object identification supplied by the computer for positioning a selected membrane of the target cell in the laser focus.

17. The apparatus according to claim 14;
wherein the image processing unit contains image processing software by which the course of the transient membrane changes can be detected.

* * * * *